(12) United States Patent
Puttachari et al.

(10) Patent No.: US 8,518,439 B2
(45) Date of Patent: Aug. 27, 2013

(54) LIQUID THERAPEUTIC COMPOSITION

(75) Inventors: Satisha Puttachari, Thane (IN);
Shripad Naik, Mumbai (IN);
Christopher Joseph Pulford, Lincoln, NE (US)

(73) Assignee: Novartis AG, Basel (CH)

( * ) Notice: Subject to any disclaimer, the term of this patent is extended or adjusted under 35 U.S.C. 154(b) by 504 days.

(21) Appl. No.: 12/630,365

(22) Filed: Dec. 3, 2009

(65) Prior Publication Data

US 2010/0136107 A1 Jun. 3, 2010

Related U.S. Application Data

(60) Provisional application No. 61/119,582, filed on Dec. 3, 2008.

(51) Int. Cl.
*A61K 31/167* (2006.01)
*A61K 31/137* (2006.01)
*A61K 31/09* (2006.01)

(52) U.S. Cl.
USPC ........................................................ 424/456

(58) Field of Classification Search
None
See application file for complete search history.

(56) References Cited

U.S. PATENT DOCUMENTS

| | | | |
|---|---|---|---|
| 4,619,934 A | 10/1986 | Sunshine et al. | |
| 4,783,465 A | 11/1988 | Sunshine et al. | |
| 4,892,877 A | 1/1990 | Sorrentino | |
| 5,013,716 A | 5/1991 | Cherukuri et al. | |
| 5,154,926 A | 10/1992 | Kawasaki et al. | |
| 5,505,961 A | 4/1996 | Shelley et al. | |
| 5,730,997 A | 3/1998 | Lienhop et al. | |
| 5,763,449 A | 6/1998 | Anaebonam et al. | |
| 5,962,461 A | 10/1999 | Anaebonam et al. | |
| 6,806,256 B2 | 10/2004 | Ulrich et al. | |
| 7,101,572 B2 | 9/2006 | Santos et al. | |
| 2002/0086878 A1 | 7/2002 | Dobrozki et al. | |
| 2003/0118613 A1* | 6/2003 | Dobrozsi et al. | 424/400 |
| 2007/0249566 A1* | 10/2007 | Martin et al. | 514/165 |
| 2007/0254027 A1* | 11/2007 | Martin et al. | 424/464 |
| 2008/0014274 A1* | 1/2008 | Bubnis et al. | 424/486 |

OTHER PUBLICATIONS

Taylor. Over-the-Counter Drug Products Intended for Oral ingestion that Contain Alcohol. Federal Register, vol. 58, No. 202, 1193, pp. 54466-54471.*

* cited by examiner

*Primary Examiner* — Susan Tran
*Assistant Examiner* — Jessica Worsham
(74) *Attorney, Agent, or Firm* — Larson & Anderson, LLC

(57) ABSTRACT

A liquid composition includes a therapeutic component dispersed in a liquid carrier system. The liquid carrier system is made up of water and a solvent. The solvent includes at least 90 wt % propylene glycol and less than 2 wt % ethanol, if ethanol is present in the solvent. The therapeutic component has acetaminophen and phenylephrine. The weight ratio of solvent to phenylephrine is between 100:1 to 2000:1. The weight ratio of solvent to acetaminophen is between 5:1 and 25:1.

17 Claims, 1 Drawing Sheet

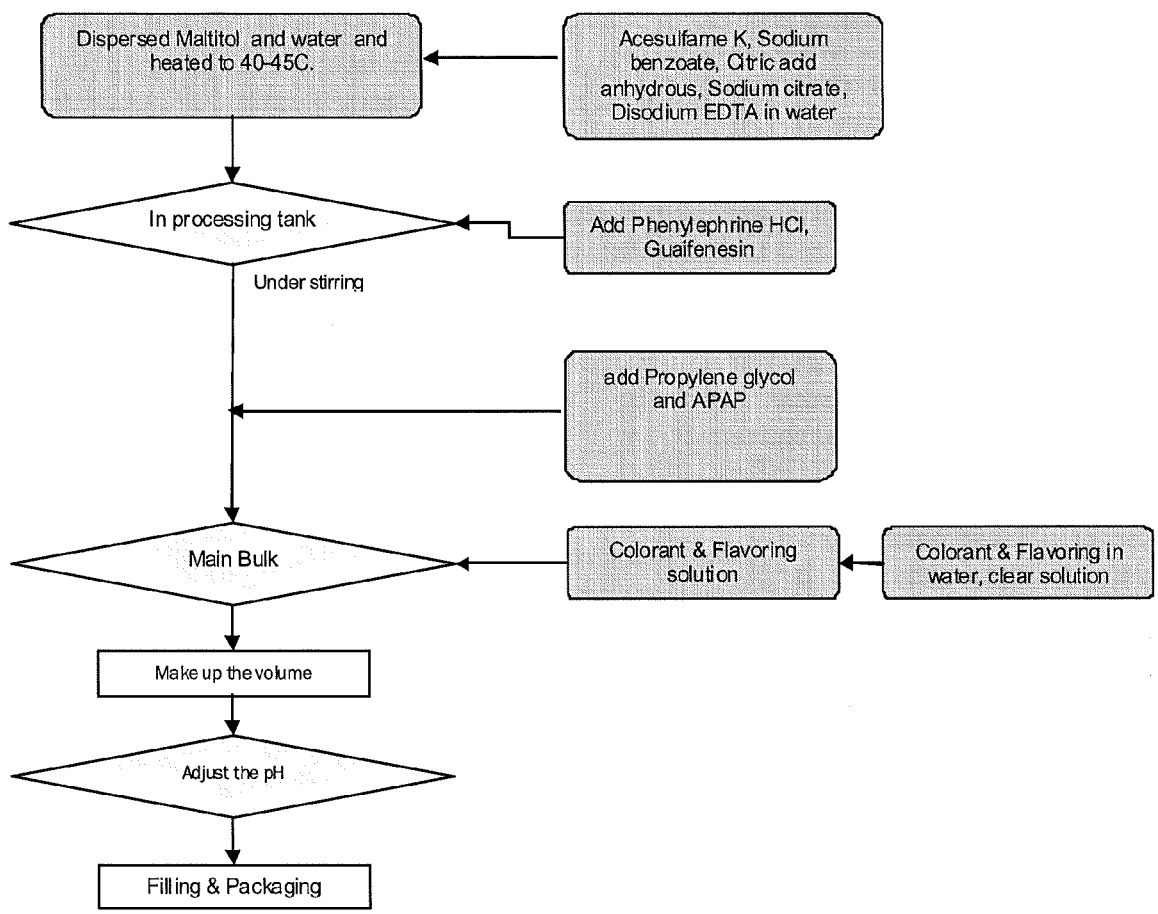

LIQUID THERAPEUTIC COMPOSITION

CROSS REFERENCE TO RELATED APPLICATION

The present application is a non-provisional application of U.S. Provisional Patent Application Ser. No. 61/119,582 which was filed on Dec. 3, 2008 and is herein incorporated by reference for all purposes.

BACKGROUND OF THE INVENTION

There are many prescription and non-prescription medications available for use in the treatment of symptoms caused by medical conditions such as colds and/or allergies (e.g. symptoms such as runny nose, fever, cough, and inflammation). In treating these symptoms it is often desirable to combine multiple pharmaceutical ingredients in a single pharmaceutically acceptable composition wherein each active ingredient is directed towards a specific symptom. However, each of the pharmaceutical ingredients generally have different physicochemical properties and stability profiles.

Patients having difficulty swallowing therapeutic compositions in tablet and/or capsule form usually prefer ingesting therapeutic compositions in liquid "syrup" dosage form. The therapeutic composition(s) is dissolved or suspended in a carrier liquid and is delivered to the patient in a measured form (e.g. in a prepackaged gel package, disposable container, or in a bottle from which the patient or care giver can measure the appropriate dosage). Syrups also are often preferred dosage forms for formulation of pharmaceutical ingredients used for the treatment of cold, cough, congestion, and fever. Furthermore, syrups which produce a warming sensation provide a sense of immediate relief to symptoms are most preferred.

Liquid therapeutic compositions have been found to degrade over time. This degradation has been found to lead to inappropriate dosing of the therapeutic agent to patients and shortened shelf life of liquid therapeutic compositions. For example, phenylephrine hydrochloride (PHL) is a decongestant frequently used in over-the-counter (OTC) cough and cold preparations. PHL is a reactive molecule that undergoes reactions with numerous carrier solvent liquids (e.g. ethanol inter alia) commonly used in OTC preparations to form other species, with a corresponding decrease in the amount of active PHL in the product. This can lead to need to set shorter expiration times than may be considered optimum for OTC products. Therefore in designing a liquid carrier composition for OTC preparations care must be taken to prevent degradation and to stabilize actives like PHL.

The formulation of clear syrups containing less soluble drugs like Acetaminophen and Guaifenesin inter alia is challenging in terms of selection of suitable solvents systems. Some of these actives are soluble in different solvents in variable amount. So it is general practice to use combination of solvents like alcohol, propylene glycol, and glycerin inter alia in combination in syrup preparation. Alcohol is a preferred solvent along with other solvents in the syrup preparations.

Furthermore, less soluble actives tend to crystallize in liquid products when it stored at lower temperatures (e.g. 5° C.) during transportation and on the shelf at the pharmacy and the home. The factors influencing the crystallization include lower temperature, lack of appropriate solvents, shaking and presence of small crystals.

While many liquid carriers have been found to be suitable for liquid preparations, many liquid carriers (e.g. ethanol) are not suitable for use in OTC liquid preparations that are intended for children. In addition, the upper limit for a OTC liquid preparations intended for adult use is 10 wt %. Therefore, there is a strong need in the OTC therapeutic liquid composition industry to provide therapeutic liquid compositions and liquid carrier systems that solve the above identified problems.

There is a need for liquid therapeutic compositions containing hard-to-dissolve actives that overcomes the problems in the art.

SUMMARY OF THE INVENTION

The present invention relates to liquid pharmaceutical compositions suitable for oral administration. The present Inventors have discovered that liquid therapeutic compositions comprising phenylephrine and acetaminophen of the present invention provide for improved stability of the liquid composition as well as increased shelf life.

In one embodiment, the present invention provides a liquid composition comprising a therapeutic component dispersed in a liquid carrier system. The liquid carrier system is made up of water and a solvent. The solvent includes at least 90 wt % propylene glycol and less than 2 wt % ethanol, if ethanol is present in the solvent. The therapeutic component has acetaminophen and phenylephrine. The weight ratio of solvent to phenylephrine is between 100:1 to 2000:1. The weight ratio of solvent to acetaminophen is between 5:1 and 25:1.

In a second embodiment, the present invention provides a method of treating a cold and/or cold-like symptoms by administering to an individual a safe and effective amount of the liquid composition described above. In a further embodiment soft gelatin capsule includes the liquid composition described above enclosed by a soft-gelatin shell.

BRIEF DESCRIPTION OF DRAWINGS

FIG. 1 is a schematic diagram showing a method of forming the liquid mixture.

DETAILED DESCRIPTION OF THE INVENTION

It has herein been found that liquid therapeutic compositions comprising phenylephrine and a hard-to-dissolve actives like acetaminophen can be preferably formulated using an aqueous liquid carrier system comprising water and a non-aqueous solvent which is predominantly propylene glycol (e.g. 100 wt % of the solvent is propylene glycol). Propylene glycol has been found to be suitable solvent for these hard-to-dissolve actives.

It has also herein been found that the liquid compositions of the present invention are unexpectedly stable over long periods of time. Without intending on being bound by a particular mechanism it is believed that by reducing the presence of ethanol in the liquid composition, one can minimize degradation of the therapeutic actives over time. Furthermore, by reducing and eliminating the ethanol in the liquid composition one can prepare a liquid therapeutic composition that has increased shelf life that can be administered to children below the age of 12.

Definitions:

"a", "an", and "the" as an antecedent refer to either the singular or plural. For example, "a therapeutic component" refers to either a single species of compound or a mixture of such species unless the context indicates otherwise.

The phrase "safe and effective amount," as used herein, is an amount that is effective to mitigate and/or treat the symptoms for which the active ingredient is indicated in a human without undue adverse side effects commensurate with a reasonable risk/benefit ratio.

The termed "dispersed" as it relates to the liquid composition (e.g. the therapeutic component "dispersed" in a liquid carrier system) is herein understood to mean that the therapeutic component dissolves, melts, suspends, or a combination thereof and distributes evenly within in the liquid carrier system.

The term "liquid carrier" refers to an aqueous liquid carrier system for the active ingredients. The aqueous liquid carrier system is made up of water and a solvent which contains at least 90 wt % (e.g. 95 wt %, 98 wt %, or more) propylene glycol. The solvent may optionally contain less than 2 wt % ethanol, however, in most preferred embodiments the solvent is free of ethanol. The term "solvent" refers to the non-aqueous portion of the liquid carrier system.

Ranges given in the specification are inclusive of either end of the specified range. For example a range of between 0.008 wt % to 0.08 wt % is inclusive of both 0.008 wt % and 0.08 wt %.

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

Numerical values in the specification and claims of this application, particularly as they relate to components of the liquid compositions, reflect average values for a composition that may contain individual components of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

The Therapeutic Component:

The therapeutic component of the liquid compositions of the present invention comprises phenylephrine and acetaminophen (also referred to as paracetamol or APAP). Phenylephrine is a decongestant compound and acetaminophen is an analgesic compound. Additional decongestants and analgesics may also be present in the therapeutic component. Examples of additional decongestants include pseudoephedrine, phenylpropanolamine, and ephedrine, their pharmaceutically acceptable salts, and mixtures thereof. Examples of additional analgesics include; morphine, codeine, meperidine, pentazocine, propoxyphene, acetaminophen, allopurinol, acetylsalicylic acid, choline salicylate, ketoprofen, magnesium silicate, fenoprofen, ibuprofen, flurbiprofen, indomethacin, naproxen, and many others and their pharmaceutically acceptable salts and mixtures thereof.

Preferably the phenylephrine is in a salt form. Suitable salt forms include, but are not limited to, phenylephrine hydrochloride (HCl), hydrobromide (HBr), bitartarate and tannate salts. Phenylephrine hydrochloride is often a preferred decongestant for OTC preparations.

It is preferred that the phenylephrine (e.g. phenylephrine hydrochloride) is present in the liquid composition such that the weight ratio of solvent to phenylephrine (e.g. phenylephrine hydrochloride) (solvent:phenylephrine) is between 100:1 to 2000:1 (more preferably between 333:1 to 1667:1).

The acetaminophen is present in the liquid composition such that the weight ratio of solvent to acetaminophen (solvent:acetaminophen) is between 5:1 and 25:1 (for example 9.2:1). In another embodiment the liquid composition comprises phenylephrine hydrochloride in an amount between 0.008 wt % to 0.08 wt % to total composition and acetaminophen in an amount between 0.33 wt % to 6.66 wt % of the total composition.

In another preferred embodiment phenylephrine hydrochloride is present in a 15 ml sample of the liquid composition of the present invention in an amount between 1 mg and 15 mg (more preferably between 2.5 and 10 mg, for example 5 mg) and acetaminophen is present in the ml sample in an amount between 50 mg and 1000 mg (more preferably between 125 mg and 500 mg, for example 325 mg).

In another embodiment the therapeutic composition of the present invention further comprises guaifenesin. Guaifenesin is an expectorant compound (also known as mucolytic agents). In a preferred embodiment, the therapeutic component comprises guaifenesin in an amount corresponding to between 0.33 wt % to 3.33 wt % of the total composition.

In a most preferred embodiment the therapeutic component of the present invention comprises phenylephrine hydrochloride, acetaminophen, and guaifenesin. In accordance with a preferred embodiment phenylephrine hydrochloride is present in the liquid composition in an amount corresponding to between 0.008 wt % to 0.08 wt % (more preferably between 0.01 wt % to 0.06 wt %) and acetaminophen is present in an amount corresponding to between 0.3 wt % to 6.6 wt % (more preferably between 0.8 wt % to 3.3 wt %). The guafenesin is preferably present in the liquid composition present in an amount corresponding to between 0.3 wt % to 3.3 wt % (more preferably between 0.6 wt % to 2.0 wt %).

The therapeutic component of the liquid compositions of the present invention may optionally further comprise an additional expectorant composition and/or an antitussive composition, an antihistamine composition, or any combination thereof.

Examples of additional expectorants include: terpin hydrate, ammonium chloride, N-acetylcysteine, and ambroxol, their pharmaceutically acceptable salts, and mixtures thereof. Examples of antitussives include dextromethorphan, chlopedianol, carbetapentane, caramiphen, noscapine, diphenhydramine, codeine, hydrocodone, hydromorphone, their pharmaceutically acceptable salts, and mixtures thereof. Dextromethorphan or diphenhydramine are often a preferred antitussives for OTC preparations.

Examples of antihistamines useful in the present invention include; brompheniramine, chlorpheniramine, clemastine, dexchlorpheniramine, diphenhydramine, doxylamine, promethazine, terfenadine, triprolidine, and many others and their pharmaceutically acceptable salts and mixtures thereof. Diphenhydramine is often a preferred antihistamine for OTC preparations.

Analgesics, decongestants, antihistamines, expectorants, and antitussives, as well as their acceptable dosage ranges are described in U.S. Pat. Nos. 4,783,465 and 4,619,934, which are incorporated by reference herein.

In another preferred embodiment the therapeutic component further comprises guaifenesin, dextromethorphan, diphenhydramine, brompheniramine, and pseudoephedrine hydrochloride.

The Liquid Carrier System:

The liquid carrier system of the liquid compositions of the present invention is an aqueous based system which includes both water (e.g. purified water) and a solvent comprising at least 90 wt % propylene glycol. In more preferred embodiments the solvent comprises more than 90 wt % propylene glycol, for example at least 95 wt % propylene glycol, like at least 98 wt % propylene glycol, and most preferably 100 wt % propylene glycol. In preferred embodiments the liquid composition contains less than 2 wt % ethanol. In a most preferred embodiment the liquid composition contain 0 wt % ethanol.

Water may be present in varying amounts and preferably makes up less than 90 wt % (for example between 60 to 80 wt %) of the liquid carrier system. In a most preferred embodiment, the liquid carrier system comprises between 60 and 80 wt % water and between 20 and 40 wt % solvent, wherein the solvent comprises at least 98 wt % propylene glycol (e.g. 100 wt % propylene glycol).

The propylene glycol is preferably a non-toxic grade of the compound and be pharmaceutically acceptable. Such pharmaceutically acceptable grades of propylene glycol are commercially available from, for example, The Dow Chemical Company.

Additive Agents:

In certain preferred embodiments the liquid composition will further comprises an additive selected from the group consisting of: a sweetener, a flavorant, a preservative, an antioxidant, and a pH stabilizer. Persons skilled in the art will quickly realize many other ingredients will be suitable for inclusion into the liquid compositions of the present invention. Other optional additives may include coloring agents, suspending agents, and releasing agents among many other agents.

In one embodiment the liquid composition comprises a flavorant dispersed in the liquid carrier system. In a preferred embodiment the flavorant comprises a warming flavor which causes warming sensation in the mouth on consumption. This gives an symptomatic relief to the patients suffering from cold and cough. The warming flavor includes a natural and/or artificial flavor optionally with added menthol. In one embodiment, the liquid composition contains an active warming flavorant in an amount corresponding to between 0.05 wt % and 0.45 wt %. A non-limiting list of exemplary warming flavorants include capsaicin, pieprine, chavicine, vanillin, vanillyl butyl ether, vanillyl ethyl ether, N-nonanoyl vanillylamide, gingerols, zingerone, and combinations of other natural and artificial flavors.

The liquid composition may further include other suitable active flavorants including orange, grape, vanilla, cherry, cranberry, peppermint, spearmint, anise, blueberry raspberry, banana, chocolate, caramel, citrus, strawberry, lemon, and lime. The addition of these type of flavorants is well known in the art and they are typically added such that the active flavor is present in the liquid composition in an amount corresponding to between 0.01 wt % and 1.0 wt % (e.g. between 0.01 and 0.12 wt %).

In a further embodiment, the liquid composition comprises a sweetener wherein the sweetener is selected from the group consisting of sucralose, saccharine salts, cyclamates, acesulfame K, dipeptide based sweeteners, and aspartame. A non-limiting list of other suitable sweetners include, dextrose, levulose, sucrose, fructose, cyclamate, mannitol, maltitol, along with many others. Sweetners are typically added such that they are present in the liquid composition in an amount sufficient to sweeten the mixture. For example artificial sweetners can be added in an amount such as 0.05 wt % to 0.5 wt % (e.g. between 0.06 wt % and 0.33 wt %) of the liquid composition while natural sweetners such as sucrose can be added in an amount up to about 82.0 wt % of the mixture.

In another embodiment, the liquid composition comprises a pH stabilizer (e.g. a buffering agent) in an amount sufficient to maintain the pH of the liquid composition at a pH of less than 6.0 and more preferably in a range of between 2.0 and 5.0. A non-limiting list of suitable buffers include sodium citrate and citric acid.

In still a further embodiment, the liquid composition comprises a preservative agent. In one embodiment the preservative is selected from the group consisting of sodium benzoate, sorbates, and parabens. Preservatives useful in the present invention include but are not limited to sodium benzoate, sorbates, such as potassium sorbate, benzaldionium chloride and parabens (such as methyl, ethyl, propyl, and butyl p-hydroxybenzoic acid esters). Preservatives listed above are exemplary, but each preservative must be evaluated on an experimental basis, in each formulation to assure compatibility and efficacy of the preservative. Methods for evaluating the efficacy of preservatives in pharmaceutical formulations are known to those skilled in the art. Sodium benzoate is the presently preferred preservative ingredient.

Preservatives are generally present in amounts of up to one gram per 100 ml of the pharmaceutical composition. Preferably the preservatives are present in amounts in the range of from about 0.01 w/v to about 0.4 w/v of the composition. Typically, the preservative sodium benzoate would be present in the range of about 0.1 w/v to about 0.2 w/v of the composition, for example. Sodium benzoate was used in a concentration of about 0.12 w/v in an exemplary embodiment of the composition.

In another embodiment, the liquid composition comprises an antioxidant wherein the antioxidant is selected from the group consisting of sodium sulphite, sodium sulphate, sodium thiosulphate, sodium metabisulphate, and propyl gallate. Antioxidants are typically added such that they are present in the liquid composition in an amount corresponding to between 0.01 wt % and 1.0 wt % (e.g. between 0.05 wt % to 0.30 wt %) of the liquid composition.

In one embodiment the liquid composition is free from benzyl alcohol. However, in another embodiment the liquid composition may further comprise benzyl alcohol as such may be present as one of the components in a selected flavorant (e.g. orange flavor).

A Method of Treating a Cold or Cold-like Symptoms:

The liquid compositions of the present invention are preferred for use in treating cold or cold-like symptoms. A person suffering from cold or cold-like symptoms may find relief by orally ingesting a safe and effective amount of the liquid compositions as described above. The safe and effective amount of liquid composition is dependent upon the concentration of the therapeutic components present in the liquid compositions. In a preferred embodiment, the safe and effective amount of liquid composition is in a range between 5 ml to 30 ml of the liquid composition.

The preferred liquid compositions comprise less than 2 wt % ethanol, and in most preferred embodiments less than 1 wt % (e.g. no ethanol or 0 wt % ethanol). These preferred compositions are safely consumed by children (e.g. individual having an age of 12 years or younger).

The method of administering the liquid composition to an individual is not particularly limited. For example, the liquid composition may be administered to an individual in liquid form (e.g. by dosage cup or reservoir such as a spoon) or it may be encapsulated in a soft gelatin capsule that is chewable or swallowable by the individual. In alternative embodiments the liquid composition may be blended with compositions such as ice, milk, soda, juice, or some other edible composition and administered to the individual.

Exemplary Method of Producing the Liquid Composition:

The methods used to prepare the liquid compositions of the present claims are not particularly limited. However, in a preferred embodiment as depicted in FIG. 1 the following steps can be used to prepare a flavored liquid composition including phenylephrine HCL, acetaminophen, and guafenesin in a liquid carrier system comprising water and propylene glycol.

(I) In a first step maltitol and water are combined in a stirred tank and heated to between 40-45° C.

(II) In a second step a mixture of acesulfame K, sodium benzoate, anhydrous citric acid, sodium citrate, disodium EDTA, and water is prepared and added to the maltitol/water mixture in step (I) and the combined mixture is then introduced to processing tank. The contents of the processing tanks are stirred continuously.

(III) In the third step phenylephrine HCL and guaifenesin are added to the stirred processing tank.

(IV) In a fourth step, propylene glycol and APAP are introduced to the components of steps (III) to form a main bulk product.

(V) In a fifth step a colorant additive agent and flavoring additive agent are prepared in an aqueous solution and subsequently added to the main bulk product produced in step (IV).

(VI) In a sixth step the main bulk is diluted to muke up the volume (e.g. by diluting with the addition either water, propylene glycol, or both water and propylene glycol) to prepare a liquid composition having the desired therapeutic component concentration.

(VII) In a seventh step, the pH of the diluted bulk prepared in step (VI) is determined. If the pH of the diluted bulk prepared in step (VI) t is outside of a predetermined range, a pH adjusting solution is added to the product in an amount to adjust the pH to within a predetermined range.

(VIII) In an eighth step the pH adjusted product prepared in step (VII) is sent to a filling and packaging station where the pH adjusted product is packaged for end consumer use.

EXAMPLES

Having described the invention in detail, the following examples are provided. The examples should not be considered as limiting the scope of the invention, but merely as illustrative and representative thereof.

The terms "working" and "comparative" are simply used to demonstrate comparisons to other examples.

Illustration 1: Physical Stability During Simulated Transportation Condition at 5° C.

Illustrations 1 and 2 make use of a working example formulation prepared in accordance with the present invention and two products made by McNeil Consumer Healthcare that are available as over-the-counter products at local pharmacies. The working example formulation contains propylene glycol as a single solvent and the Tylenol® products contain a mixture of solvents including propylene glycol and glycerin.

The working example formulation was prepared using good manufacturing practices (GMP) and packaged into 8 fluid once bottles for testing. The contents include:

| Name of the material | Working Example (mg/30 ml) |
| --- | --- |
| Phenylephrine HCl (USP) | 10 |
| Acetaminophen Powder | 650 |
| Guaifenesin USP | 400 |
| Maltitol Solution (NF) | 18000 |
| Sodium Benzoate (NF) | 35.4 |
| Edetate Disodium (USP) | 30 |
| Sodium Citrate (USP) | 25.27 |
| Citric Acid (USP) | 85.83 |
| Propylene Glycol (USP) | 6000 |
| Acesulfame K | 33.5 |
| Sensate Flavor | 45 |
| FD&C Yellow No. 6 | 19.5 |
| Orange flavour | 12 |
| Purified Water (USP) | q.s. to 30 ml |

The two over-the-counter products are available under the trade names Tylenol® Cold Multi-Symptom Daytime (e.g. Tylenol® NS) and Tylenol® Cold Multi-Symptom Severe (e.g. Tylenol® S). These products were purchased and tested in their respective 8 ounce bottles. Tylenol® NS lists ingredients including:

Active Ingredients per 15 ml sample:
Acetaminophen (325 mg), Dextromethorphan HBr (10 mg), and Phenylephrine HCI (5 mg).
Inactive Ingredients:
Citric Acid, Ethyl Alcohol, FD&C Yellow 6, Flavors, Glycerin, Propylene Glycol, Purified Water, Sodium Benzoate, Sorbitol, and Sucralose.

Tylenol® S lists ingredients including:
Active Ingredients per 15 ml sample:
Acetaminophen (325 mg), Guaifenesin (200 mg), Dextromethorphan HBr (10 mg), and Phenylephrine HCI (5 mg).
Inactive Ingredients: Anhydrous Citric Acid, Ethyl Alcohol, FD&C Blue 1, Flavor, Glycerin, Propylene Glycol, Purified Water, Sodium Benzoate, Sorbitol Solution, and Sucralose The objective of this illustration is to assess the comparative physical stability of the formulations under conditions simulating product transportation at 5° C.

The bottles were attached to mechanical shaker and kept in chambers controlled at 5° C. The samples were shaken continuously using a mechanical shaker to simulate the agitation of transportation.

TABLE 1

| Day of observation | Working Example | Tylenol NS | Tylenol S |
| --- | --- | --- | --- |
| Zero day | No Crystals | No Crystals | No Crystals |
| 2 days | No Crystals | No Crystals | No Crystals |
| 5 days | No Crystals | No Crystals | No Crystals |
| 7 days | No Crystals | No Crystals | No Crystals |
| 9 days | No Crystals | No Crystals | No Crystals |
| 12 days | No Crystals | No Crystals | No Crystals |
| 14 days | No Crystals | No Crystals | No Crystals |
| 16 days | No Crystals | No Crystals | No Crystals |
| 19 days | No Crystals | No Crystals | No Crystals |
| 21 days | No Crystals | No Crystals | No Crystals |
| 23 days | No Crystals | No Crystals | No Crystals |
| 27 days | No Crystals | No Crystals | No Crystals |
| 30 days | No Crystals | No Crystals | No Crystals |
| 34 days | No Crystals | No Crystals | No Crystals |

The results show that the tested formulations exhibit similar stability under conditions simulating transportation in unopened bottles.

Illustration 2: Physical Stability of Samples in the Condition of "In-use Study"

The objective of this illustration is to demonstrate the physical stability of the formulations under conditions simulating in-use situations.

The three formulations described above (Working Example, Tylenol® NS, and Tylenol® S) were used. They were subjected to 5 different studies. In each of the 5 studies, each formulation was tested three times (e.g. three separate 8 ounce bottles). The details of the studies are as follows:

Trial 1. The samples were kept at 50° C. in unopened 8 ounce bottles;

Trial 2. The caps of the 8 ounce bottles were removed and kept at 50° C.;

Trial 3. Four doses were removed and the 8 ounce bottle was stored in a refrigerator, after two weeks two more doses were removed and the bottle was again stored in a refrigerator;

Trial 4. Five doses were removed on day zero at regular intervals from the bottle and the bottle was stored in a refrigerator; and Trial 5. Removed one dose per day for 5 days from the bottle and then stored in a refrigerator.

The samples were checked for the appearance of crystals at frequent intervals. The results are shown in Tables 2 and 3.

TABLE 2

| Trial | Example | Day Zero | Day 3 | Day 5 | Day 9 | Day 11 | Day 13 | Day 15 | Day 18 | Day 20 | Day 22 | Day 27 | Day 30 | Day 33 |
|---|---|---|---|---|---|---|---|---|---|---|---|---|---|---|
| Trial 1: Unopened bottles* | Working Example | No Crystals | No Crystals | No Crystals | No Crystals | No Crystals | No Crystals | No Crystals | No Crystals | No Crystals | No Crystals | No Crystals | No Crystals | No Crystals |
| | Tylenol NS | No Crystals | No Crystals | No Crystals | No Crystals | No Crystals | No Crystals | No Crystals | No Crystals | No Crystals | No Crystals | No Crystals | No Crystals | No Crystals |
| | Tylenol S | No Crystals | No Crystals | No Crystals | No Crystals | No Crystals | No Crystals | No Crystals | No Crystals | No Crystals | No Crystals | No Crystals | No Crystals | No Crystals |
| Trial 2: Opened bottles* | Working Example | No Crystals | No Crystals | No Crystals | No Crystals | No Crystals | No Crystals | No Crystals | No Crystals | No Crystals | No Crystals | No Crystals | No Crystals | No Crystals |
| | Tylenol NS | No Crystals | No Crystals | No Crystals | No Crystals | No Crystals | No Crystals | No Crystals | No Crystals | No Crystals | No Crystals | No Crystals | No Crystals | No Crystals |
| | Tylenol S | No Crystals | No Crystals | No Crystals | No Crystals | No Crystals | No Crystals | No Crystals | No Crystals | No Crystals | No Crystals | No Crystals | No Crystals | No Crystals |

TABLE 3

| Trial | Example | Day Zero | Day 3 | Day 5 | Day 9 | Day 11 | Day 13 | Day 15 |
|---|---|---|---|---|---|---|---|---|
| Trial 3: Removed 4 doses and stored in fridge. After 2 weeks removed 2 more doses and stored in fridge. | Working Example | No Crystals | No Crystals | No Crystals | Minute crystals in 1 bottle | Minute crystals in 1 bottle | Minute crystals in 1 bottle | Minute crystals in 1 bottle |
| | Tylenol NS | No Crystals | No Crystals | No Crystals | One large crystal in 1 bottle | One large crystal in 1 bottle | One large crystal in 1 bottle | Crystals in 1 bottle |
| | Tylenol S | No Crystals | No Crystals | No Crystals | No Crystals | No Crystals | One large crystal in 1 bottle | One large crystal in 1 bottle |
| Trial 4: Removed 5 doses in a same day at regular intervals and stored in fridge | Working Example | No Crystals | No Crystals | No Crystals | No Crystals | No Crystals | No Crystals | No Crystals |
| | Tylenol NS | Crystals | Crystals in 1 bottle | Crystals in all 3 bottles | Crystals in all 3 bottles | Crystals in all 3 bottles | Crystals in all 3 bottles | Crystals in all 3 bottles |
| | Tylenol S | No Crystals | Slight crystals in 2 bottles | Slight crystals in 2 bottles | Slight crystals in 2 bottles | Slight crystals in 2 bottles | Crystals in 2 bottles | Crystals in 2 bottles |
| Trial 5: Removed 1 dose a day for 5 days and stored in fridge1, 2 | Working Example | No Crystals | Crystals in 2 bottles | Crystals in 2 bottles | Crystals in 2 bottles | Crystals in 2 bottles | Crystals in 2 bottles | Crystals in 2 bottles |
| | Tylenol NS | Crystals | Crystals in 1 bottle | Crystals in 2 bottles | Crystals in 3 bottles | Crystals in all 3 bottles | Crystals in all 3 bottles | Crystals in 3 bottles | Crystals in 3 bottles |
| | Tylenol S | No Crystals | Slight crystals in 2 bottles | Slight crystals in all 3 bottles | Slight crystals in all 3 bottles | Slight crystals in all 3 bottles | Crystals in 3 bottles | Crystals in 3 bottles |

| Trial | Example | Day 18 | Day 20 | Day 22 | Day 27 | Day 30 | Day 33 |
|---|---|---|---|---|---|---|---|
| Trial 3: Removed 4 doses and stored in fridge. | Working Example | Minute crystals in 2 bottles | Minute crystals in 2 bottles | Minute crystals in 2 bottles | Minute crystals in 2 bottles | Minute crystals in 2 bottles | Crystals in 2 bottles |
| | Tylenol NS | Crystals in all 3 | Crystals in all 3 | Crystals in all 3 | Crystals in all 3 | Crystals in all 3 | Crystals in all 3 |

TABLE 3-continued

| After 2 weeks removed 2 more doses and stored in fridge. | Tylenol S | bottles One large crystal in 1 bottle | bottles Crystal in 2 bottles | bottles Crystal in 2 bottles | bottles Crystal in 2 bottles | bottles Crystal in 2 bottles | bottles Crystal in 2 bottles |
|---|---|---|---|---|---|---|---|
| Trial 4: Removed 5 doses in a same day at regular intervals and stored in fridge | Working Example | No Crystals | No Crystals | No Crystals | No Crystals | No Crystals | No Crystals |
| | Tylenol NS | Crystals in all 3 bottles | Crystals in all 3 bottles | Crystals in all 3 bottles | Crystals in all 3 bottles | Crystals in all 3 bottles | Crystals in all 3 bottles |
| | Tylenol S | Crystals in all 3 bottles | Crystals in all 3 bottles | Crystals in all 3 bottles | Crystals in all 3 bottles | Crystals in all 3 bottles | Crystals in all 3 bottles |
| Trial 5: Removed 1 dose a day for 5 days and stored in fridge1, 2 | Working Example | Crystals in all 3 bottles | Crystals in all 3 bottles | Crystals in all 3 bottles | Crystals in all 3 bottles | Crystals in all 3 bottles | Crystals in all 3 bottles |
| | Tylenol NS | Crystals in all 3 bottles | Crystals in all 3 bottles | Crystals in all 3 bottles | Crystals in all 3 bottles | Crystals in all 3 bottles | Crystals in all 3 bottles |
| | Tylenol S | Crystals in all 3 bottles | Crystals in all 3 bottles | Crystals in all 3 bottles | Crystals in all 3 bottles | Crystals in all 3 bottles | Crystals in all 3 bottles |

The overall physical stability of the formulations in the above 5 trials showed that of the tested products having the Working Example formulation with propylene glycol comprising at least 90 wt % of the solvent system (e.g. more than 95 and 98 wt % of the solvent system) had a preferable stability profile as compared to the Tylenol products having multiple ingredient solvent system different than that of the present invention.

Illustration 3: Long Term Stability Studies as Per ICH Stability Testing

The objective of this illustration is to demonstrate the stability of active ingredients (e.g. Acetaminophen and Phenylephrine HCL) of the formulations under various conditions. The components of the formulations are shown in Table 4 and the test conditions and results are shown in Tables 5 and 6.

TABLE 4

| Formulations Tested | | |
|---|---|---|
| Name of the material | Working Example with 15% PG | Working Example with 20% PG |
| Phenylephrine HCl (USP) | 10 | 10 |
| Acetaminophen Powder | 650 | 650 |
| Guaifenesin USP | 400 | 400 |
| Maltitol Solution (NF) | 18000 | 18000 |
| Sodium Benzoate (NF) | 35.4 | 35.4 |
| Edetate Disodium (USP) | 30 | 30 |
| Sodium Citrate (USP) | 25.27 | 25.27 |
| Citric Acid (USP) | 85.83 | 85.83 |
| Propylene Glycol (USP) | 4500 | 6000 |
| Acesulfame K | 33.5 | 33.5 |
| Sensate Flavor | 45 | 45 |
| FD&C Yellow No. 6 | 19.5 | 19.5 |
| Orange flavour | 12 | 12 |
| Purified Water (USP) | q.s. to 30 ml | q.s. to 30 ml |

TABLE 5

| Stability condition | Stability duration | WE with 15% PG | | WE with 20% PG | |
|---|---|---|---|---|---|
| | | % Assay of APAP | % Assay of PHL | % Assay of APAP | % Assay of PHL |
| Initial | 0 | 100.3 | 99.8 | 101.3 | 100.6 |
| 40° C./75% RH | 1 M | 101.2 | 97.1 | 101.5 | 99.7 |
| 40° C./75% RH | 2 M | 100.8 | 99 | | |
| 40° C./75% RH | 3 M | 101.6 | 98.8 | 101.3 | 99.8 |
| 40° C./75% RH | 6 M | 101.8 | 95.9 | 99.9 | 98 |
| 50° C. | 1 M | 101.1 | 96.8 | 101.8 | 97.9 |
| 25° C./60% RH | 6 M | 101.9 | 100.6 | 100 | 100.6 |
| 25° C./60% RH | 12 M | — | — | 102.3 | 98 |
| 30° C./75% RH | 6 M | — | — | 99.8 | 99.4 |
| 30° C./75% RH | 12 M | — | — | 101.7 | 95.6 |
| FT/3 Cycles | | 99.7 | 99.8 | 102.2 | 101.9 |

TABLE 6

| Stability condition | Stability duration | WE with 15% PG | | WE with 20% PG | |
|---|---|---|---|---|---|
| | | % Imp of APAP | % Imp of PHL | % Imp of APAP | % Imp of PHL |
| Initial | 0 | 0.03 | 0.59 | 0.04 | 0.63 |
| 40° C./75% RH | 1 M | 0.01 | 1.78 | 0.02 | 0.66 |
| 40° C./75% RH | 2 M | 0.04 | 1.2 | — | — |
| 40° C./75% RH | 3 M | 0.09 | 1.72 | 0.08 | 1.33 |

TABLE 6-continued

| | | WE with 15% PG | | WE with 20% PG | |
|---|---|---|---|---|---|
| Stability condition | Stability duration | % Imp of APAP | % Imp of PHL | % Imp of APAP | % Imp of PHL |
| 40° C./75% RH | 6 M | 0.07 | 2.9 | 0.11 | 2.69 |
| 50° C. | 1 M | 0.05 | 2.08 | — | — |
| 25° C./60% RH | 6 M | 0.03 | 1.09 | 0.03 | 1.14 |
| 25° C./60% RH | 12 M | — | — | 0 | 1 |
| 30° C./75% RH | 6 M | — | — | 0 | 1.36 |
| 30° C./75% RH | 12 M | — | — | 0 | 1.46 |
| FT/3 Cycles | 3 Cycles | 0.03 | 1.86 | 0.04 | 0.76 |

— The samples were not analysed
WE Working Example
PG Propylene Glycol
APAP Acetaminophen
PHL Phenylephrine hydrochloride
FT/3 Cycle Freeze Thaw 3 cycles
RH Relative Humidity The Working Example (WE) with 15% PG contained between about 7 and 9 ml of additional water per 30 ml. The WE with 20% PG contained between about 5 and 7 ml of additional water. The formulations also include maltitol dispersed in about 30 wt % water. The total water in the WE with 15% PG therefore contained about 57 to 60 wt % water and the WE with 20 wt % PG formulation contained about 47 to 57% water.

The FT/3 Cycle experimental condition was carried out by subjecting the formulations at −20° C. for 5 days and 25° C. at 60% RH for 1 day. This completed one cycle. The samples were subjected to 3 freeze/thaw cycles.

% Imp of APAP refers to total impurities of acetaminophen (APAP) and % Imp of phenylephrine hydrochloride (PHL) refers to total impurities of PHL. It is believed that these values changed over time as impurities are generated at stressed conditions due to interaction with excipients and other actives. The values were determined using chromotographic testing techniques and referenced against known standards.

% Assay of APAP refers to % Assay (content) of APAP and % Assay of PHL refer to % Assay of Phenylephrine HCl. It is believed that these values change over time as it is degraded to form other compounds. The values were determined using chromotographic testing techniques and referenced against known standards.

There was some discrepancy observed in the % assay of APAP (e.g. % assay increased on stability in some of the cases). Without being bound by a particular mechanism, it is believed this increase is due to variation in testing equipment calibration and the value is within normal testing variation (e.g within about 2.0%).

This illustration demonstrates, inter alia, that the formulations of the present invention provide for minimal degradation of the APAP and PHL in the composition.

The invention claimed is:

1. A liquid composition comprising a therapeutic component dispersed in a liquid carrier system, wherein:
the liquid carrier system comprises water and a solvent,
the solvent comprises at least 90 wt % propylene glycol and less than 2 wt % ethanol, if ethanol is present in the solvent, and
the therapeutic component comprises acetaminophen and phenylephrine,
the weight ratio of solvent to phenylephrine is between 100:1 to 2000:1, and
the weight ratio of solvent to acetaminophen is between 5:1 and 25:1.

2. The liquid composition of claim 1, wherein the solvent comprises 95 wt % propylene glycol.

3. The liquid composition of claim 2, wherein the solvent comprises 98 wt % propylene glycol.

4. The liquid composition of claim 3, wherein the solvent comprises 100 wt % propylene glycol.

5. The liquid composition of claim 3, wherein the solvent is free of ethanol.

6. The liquid composition of claim 3, wherein the therapeutic component further comprises guaifenesin in an amount corresponding to between 0.33 wt % to 3.33 wt % of the total composition.

7. The liquid composition of claim 6, wherein the therapeutic component further comprises a compound selected from the group consisting of dextromethorphan, diphenhydramine, brompheniramine, and pseudoephedrine.

8. The liquid composition of claim 3, wherein phenylephrine is present in salt form wherein the salt of phenylephrine is selected from the group consisting of phenylephrine hydrochloride, phenylephrine hydrobromide, phenylephrine bitartarate, and phenylephrine tannate.

9. The liquid composition of claim 8, wherein the therapeutic component comprises phenylephrine hydrochloride such that the weight ratio of solvent to phenylephrine hydrochloride (solvent:phenylephrine hydrochloride) is between 333:1 to 1667:1.

10. The liquid composition of claim 8, wherein the therapeutic component comprises phenylephrine hydrochloride in an amount between 0.008 wt % to 0.08 wt % of the total composition and acetaminophen in an amount between 0.33 wt % to 6.66 wt % of the total composition.

11. The liquid composition of claim 3, further comprising an additive selected from the group consisting of a sweetener, a flavorant, a preservative, an antioxidant, and a pH stabilizer.

12. The liquid composition of claim 3, further comprising a flavorant and a pH stabilizer, wherein the flavorant comprises a warming flavor and the pH stabilizer is present in an amount sufficient to maintain the pH of the liquid composition in a range of between 2.0 and 5.0.

13. The liquid composition of claim 3, wherein the liquid carrier system comprises 60 to 80 wt % water and 20 to 40 wt % of the solvent.

14. A method of treating a cold or cold-like symptoms in an individual, wherein the method comprises administering to the individual a safe and effective amount of a liquid composition comprising a therapeutic component dispersed in a liquid carrier system, wherein:
the liquid carrier system comprises water and a solvent,
the solvent comprises at least 90 wt % propylene glycol and less than 2 wt % ethanol, if ethanol is present in the solvent, and
the therapeutic component comprises acetaminophen and phenylephrine,
the weight ratio of solvent to phenylephrine is between 100:1 to 2000:1, and
the weight ratio of solvent to acetaminophen is between 5:1 and 25:1.

15. The method of claim 14, wherein the safe and effective amount of the liquid composition is in a range between 5 ml to 30 ml of the liquid composition.

16. The method of claim 14, wherein the individual is 12 years of age or younger.

17. A soft gelatin capsule comprising a soft gelatin shell and between 5 ml and 30 ml of a liquid composition comprising a therapeutic component dispersed in a liquid carrier system, wherein:

the liquid carrier system comprises water and a solvent, the solvent comprises at least 90 wt % propylene glycol and less than 2 wt % ethanol, if ethanol is present in the solvent, and the therapeutic component comprises acetaminophen and phenylephrine, the weight ratio of solvent to phenylephrine is between 100:1 to 2000:1, and the weight ratio of solvent to acetaminophen is between 5:1 and 25:1, wherein the liquid composition is enclosed by the soft gelatin shell.

* * * * *